US00PP13138P2

(12) United States Plant Patent
Olesen et al.

(10) Patent No.: US PP13,138 P2
(45) Date of Patent: Oct. 29, 2002

(54) MINIATURE ROSE PLANT NAMED 'POULROLYT'

(76) Inventors: L. Pernille Olesen, Hillerødvejen 49, DK-3480 Fredensborg (DK); Mogens N. Olesen, Hillerødvejen 49, DK-3480 Fredensborg (DK)

( * ) Notice: Subject to any disclaimer, the term of this patent is extended or adjusted under 35 U.S.C. 154(b) by 23 days.

(21) Appl. No.: 09/655,263

(22) Filed: Sep. 5, 2000

(51) Int. Cl.[7] ..... A01H 5/00
(52) U.S. Cl. ..... Plt./122
(58) Field of Search ..... Plt./122, 121, 116

(56) References Cited

U.S. PATENT DOCUMENTS

PP9,483 P * 3/1996 Olesen et al. ..... Plt./122

OTHER PUBLICATIONS

Community Plant Variety Office. "Certificate on the Grant of Community Plant Variety Rights" Jun. 19, 2000. 6 pages. EU.

UPOV–ROM 2001/03, Plant Variety Database, GTI Jouve Retrieval Software, 2 citations for 'POULroyt'.*

Cooper, "Biotechnology and the Law", (Clark Boardman Callaghan) vol. 2, 2000 Revision, pp. 8–15 to 8–16.*

* cited by examiner

*Primary Examiner*—Howard J. Locker

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and 'POULhappy' (U.S. Plant Pat. No. 9,483, dated Mar. 26, 1996). The two parents were crossed and the resulting seeds were planted in a controlled environment. The new variety is named 'POULrolyt'. The new rose may be distinguished from its seed parent, an unnamed seedling, by the following combination of characteristics:

1. The unnamed seed parent is a miniature rose with dark red flowers, while POULrolyt has brighter, red flowers.

The new variety may be distinguished from its pollen parent, 'POULhappy', created by the same inventors, by the following combination of characteristics:

1. 'POULhappy' has smaller flowers than 'POULrolyt'.

2. 'POULhappy' has more numerous flowers than 'POULrolyt'.

The objective of the hybridization of this rose variety for commercial culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

The combination of qualities of this variety represents significant improvement over previously available commercial cultivars of this type and distinguishes 'POULrolyt' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark.

'POULrolyt' was selected by the inventors as a single plant from the progeny of the hybridization in Fredensborg, Denmark.

Asexual reproduction of 'POULrolyt' by cuttings and traditional budding onto *Rosa multiflora* understock was first done by L. Pernille and Mogens N. Olesen in Fredensborg, Denmark. This initial and other subsequent propagations conducted in controlled environments have demonstrated that the characteristics of 'POULrolyt' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULrolyt'. Specifically illustrated in SHEET 1:

1. A flowering stem showing branching and the attachment of leaves, buds, and peduncles;

2. Flower bud, partially opened bud, and open bloom;

3. Flower petals, detached;

4. Sepals, receptacle, and pedicel;

5. A partly foliated stem as well as a bare stem exhibiting thorns;

6. Leaves.

DETAILED DESCRIPTION OF THE VARIETY

The following is a description of 'POULrolyt', as observed in its growth in glasshouses in Half Moon Bay, Calif. Color references are made using The Royal Horticultural Society (London, England) Colour Chart, 1995, except where common terms of color are used.

For a comparison, several physical characteristics of the rose variety 'POULrouge', a miniature rose variety from the same inventors described and illustrated in U.S. Plant Pat. No. 9,687 and issued on Nov. 12, 1996 are compared to 'POULrolyt' in Chart 1.

CHART 1

| | 'POULrolyt' | 'POULrouge' |
|---|---|---|
| Petal Color, Upper Side: | Red Group 50A | Red Group 40B |
| Petal Color, Reverse Side: | Red Group 58B | Red Group 41B |
| Basal Petal Spot: | White Group 155C | Yellow Group 7D |

Parents: Unnamed Seedling×POULhappy

Classification:

*Botanical.*—*Rosa hybrida.*

*Commercial.*—Miniature.

FLOWER AND FLOWER BUD

Blooming habit: Recurrent.

Flower bud:

*Size.*—Upon opening, 20 mm–23 mm in length from base of receptacle to end of bud.

*Bud form.*—Long; pointed ovoid.

*Bud color.*—As sepals unfold Red Group 50B, Red Group 50B at ¼ opening.

*Sepals.*—Yellow Green Group 143B. Weak foliaceous appendages on three of the five sepals. Surfaces of sepals moderately pubescent. Stipitate glands are moderately present on outer surface of sepal.

*Receptacle.*—Surface: Smooth. Shape: Funnel-shaped. Size: 5 mm (h)×7 mm (w). Color: Yellow Green Group 144A.

*Peduncle.*—Surface: Smooth. Length: 30 to 40 mm average length. Color: Yellow-Green Group 144A. Strength: Upright.

*Borne.*—Generally with 3 to 4 buds per flowering stem.

Flower bloom:

*Fragrance.*—None.

*Duration.*—As a pot plant, flowers last from 6 to 8 days. As a cut flower 4 to 5 days.

*Size.*—Medium for a 12.5 cm pot rose. Average flower diameter is 40 mm when open.

*Form.*—Shape of flower when viewed from the side: Upon opening, upper part: Flattened convex. Upon opening, lower part: Flattened convex. Open flower, upper part: Convex. Open flower, lower part: Flattened convex.

*Petalage.*—Average range: 30 to 35 petals under normal conditions with 1 to 3 petaloids.

Color:

*Upon opening, petals.*—Outermost petals: Upper Surface: Red Group 50A, with occasional variegation in the form of a central striation, White Group 155A. Reverse Side: Red-Purple Group 58B. Innermost petals: Upper Surface: Red-Purple Group 58B–C with occasional variegation in the form of a central striation, White Group 155A. Reverse Side: Red-Purple Group 57C.

*Upon opening, basal petal spots.*—Outermost petals: Outer Side: White Group 155C. Inner Side: White Group 155C. Innermost petals: Outer Side: White Group 155C. Inner Side: White Group 155C.

*After opening, petals.*—Outermost petals: Upper Surface: Red Group 50A. Reverse Side: Red Group 57D. Innermost petals: Upper Surface: Red Group 51A. Reverse Side: Red Group 57D.

*After opening, basal petal spots.*—Outermost petals: Outer Side: White Group 155C. Inner Side: White Group 155C. Innermost petals: Outer Side: White Group 155C. Inner Side: White Group 155C.

General tonality: On open flower Red Group 50A, with intonations of Red Group 58 B–C. No change in the general tonality at the end of the $7^{th}$ day. Afterwards, general tonality is Red Group 50B–C.

Petals:

*Petal reflex.*—Guard petals reflexed strongly; inner petals less reflexed.

*Petal edge.*—Uniform.

*Shape.*—Ovoid.

*Petaloids.*—1 to 3.

*Texture.*—Thick.

*Arrangement.*—Imbricated.

Reproductive organs:

*Pollen.*—None observed.

*Anthers.*—Size: Small. Color: Anthers are Greyed-Orange Group 166A in center, and Greyed-Orange Group 163A on margins. Abundance: Average.

*Filaments.*—Color: Greyed-Green Group 192A–B.

*Stigmas.*—Notably superior in location to anthers. Color: Greyed-Yellow Group 160A.

*Styles.*—Color: Greyed-White Group 157A.

PLANT

Plant growth: Vigorous, compact, upright to bushy. When grown in a 12.5 cm pot (as is typical in the commercial production of the variety), the average height of the plant is 20 to 30 cm and the average width is 22 to 27 cm.

Stems:

*Color.*—Young wood: Yellow-Green Group 144A Older wood: Yellow-Green Group 144A.

*Prickles.*—Incidence: 5 to 7 per 10 cm of stem. Size: Average length: 3 mm–4 mm. Color: Yellow Green Group 145A–B. Shape: Linear.

*Surface.*—Yound wood: Smooth. Older wood: Smooth.

Plant foliage: Normal number of leaflets on normal leaves in middle of the stem: 5 leaflets.

*Leaf size.*—32 mm (l)×18 mm (w).

*Abundance.*—Average.

*Color.*—Upper Leaf Surface: Green Group 139A. Lower Leaf Surface: Green Group 137B. Juvenile foliage: Green Group 137B. Anthocyanin intonation: Location: Present on juvenile foliage, on upper and lower surfaces of leaflet margins. Color: Red-Purple Group 59A.

Plant leaves and leaflets:

*Stipules.*—Size: 4 mm–6 mm. Color: Green Group 137A. Stipitate glands present on edges of stipule margins.

*Petiole.*—Length: 15 mm–30 mm. Color: Green Group 137C. Underneath: Yellow Green Group 144A.

*Rachis.*—Color: Green Group 137C. Underneath: Yellow Green Group 144A.

*Leaflet.*—Edge: Serrated. Shape: Ovate. Texture: Thin, moderately glossy.

Disease resistance: Average resistance to mildew, black spot, and Botrytis under normal growing conditions in Half Moon Bay, Calif.

Cold hardiness: 'POULrolyt' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, red flowers, vigorous and compact growth, year round flowering under glasshouse conditions, suitability for production from softwood cuttings in pots, and durable flowers and foliage which make the variety suitable for distribution in the floral industry.

* * * * *

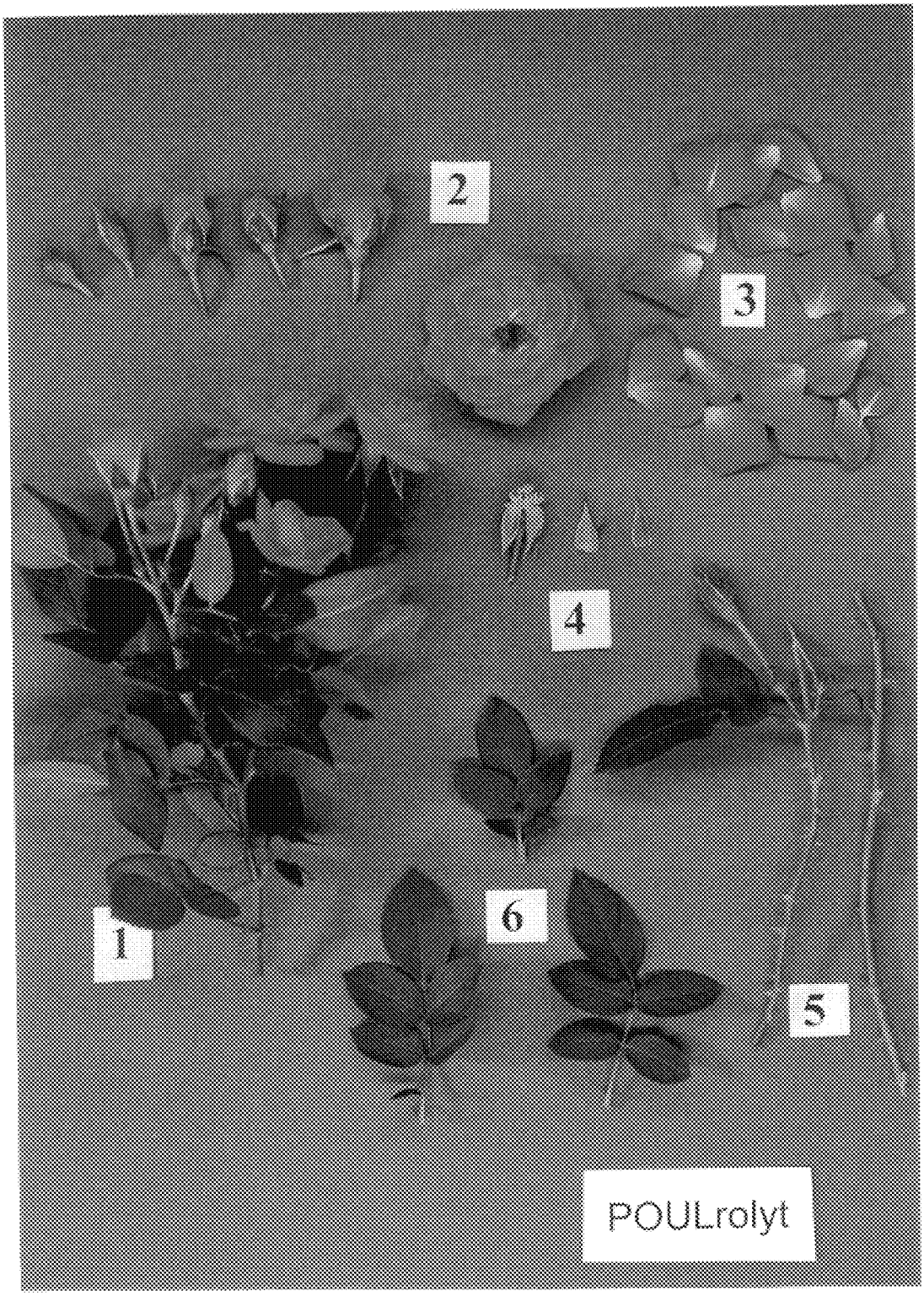
2
3
4
1
6
5
POULrolyt